(12) United States Patent
Morosawa et al.

(10) Patent No.: US 7,835,010 B2
(45) Date of Patent: Nov. 16, 2010

(54) OPTICAL COHERENCE TOMOGRAPHY SYSTEM AND OPTICAL COHERENCE TOMOGRAPHY METHOD

(75) Inventors: Atsushi Morosawa, Aichi (JP); Changho Chong, Aichi (JP)

(73) Assignee: Santec Corporation, Komaki (JP)

( * ) Notice: Subject to any disclaimer, the term of this patent is extended or adjusted under 35 U.S.C. 154(b) by 311 days.

(21) Appl. No.: 12/078,960

(22) Filed: Apr. 8, 2008

(65) Prior Publication Data

US 2008/0252899 A1 Oct. 16, 2008

(30) Foreign Application Priority Data

Apr. 13, 2007 (JP) ............................. 2007-105749

(51) Int. Cl.
*G01B 9/02* (2006.01)

(52) U.S. Cl. ...................................... 356/479; 356/484

(58) Field of Classification Search ................. 356/479, 356/484, 497; 250/227.19, 227.27
See application file for complete search history.

(56) References Cited

U.S. PATENT DOCUMENTS

2006/0244973 A1* 11/2006 Yun et al. .................... 356/511

2008/0159468 A1* 7/2008 Chong ............................ 378/4
2009/0021746 A1* 1/2009 Toida et al. .................. 356/484

OTHER PUBLICATIONS

Hee, M., "Optical Coherence Tomography: Theory", Handbook of Optical Coherence Tomography, 2002, pp. 41-66, Mercel Decker, Inc.
Huber, R. et al., "Three-Dimensional and C-mode OCT imaging With A Compact, Frequency Swept Laser Source at 1300 nm", Optics Express, Dec. 2005, 16 pages, vol. 13, No. 26.

* cited by examiner

*Primary Examiner*—Michael A Lyons
(74) *Attorney, Agent, or Firm*—Smith Patent Office

(57) ABSTRACT

A tunable light source 10 for varying emission wavelength periodically and an optical interferometer are used. A reflector is disposed at a measurement position, a light interference signal is A/D converted at a regular time interval, and data numbers at timing giving peak and bottom are calculated according to a least-squares method. Based on this, an approximate equation is calculated according to polynomial approximation and a sequence including the number of exponentiation of 2 and converting the data number at a regular frequency interval is calculated. Then, by disposing a measured target at the measurement position, calculating the necessary number of pieces of data for FFT from measured data at each timing according to straight-line approximation and Fourier transforming a light beat signal obtained by an optical interferometer at regular frequency interval, a tomogram having high resolution and high sensitivity can be acquired.

10 Claims, 10 Drawing Sheets

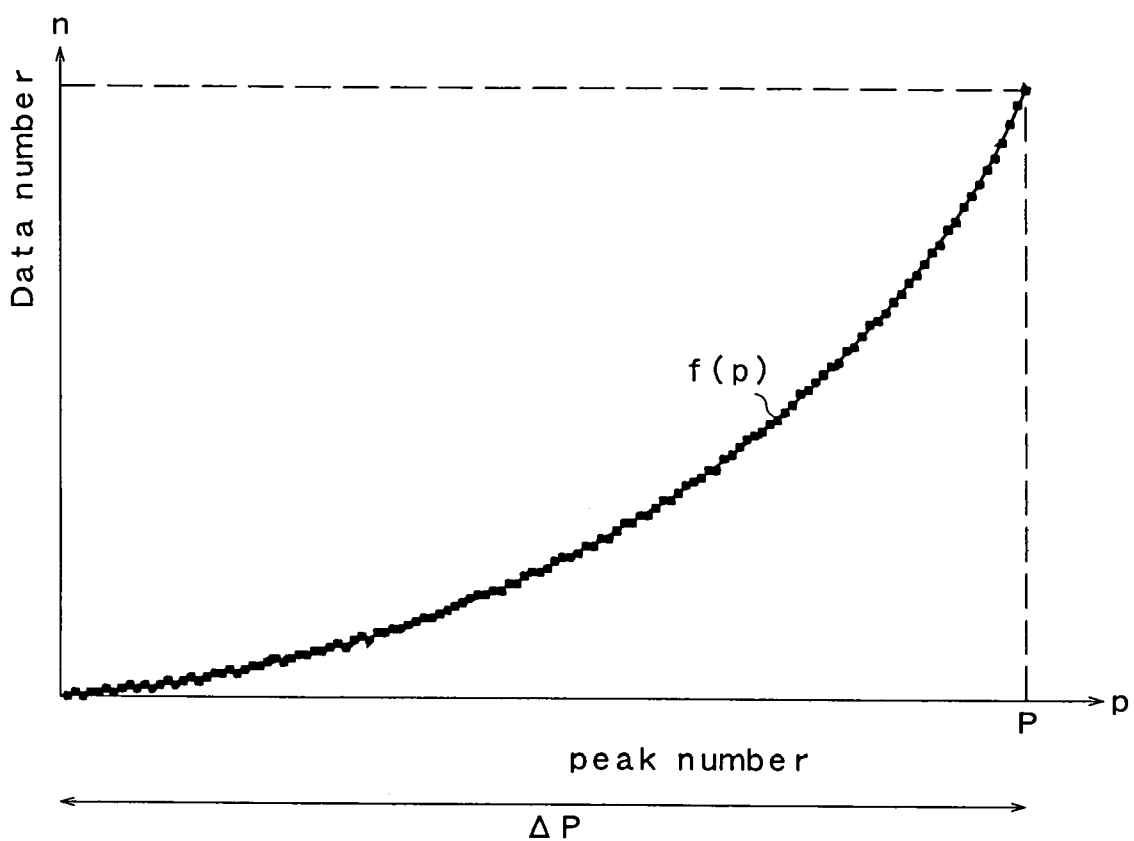

F I G. 6A
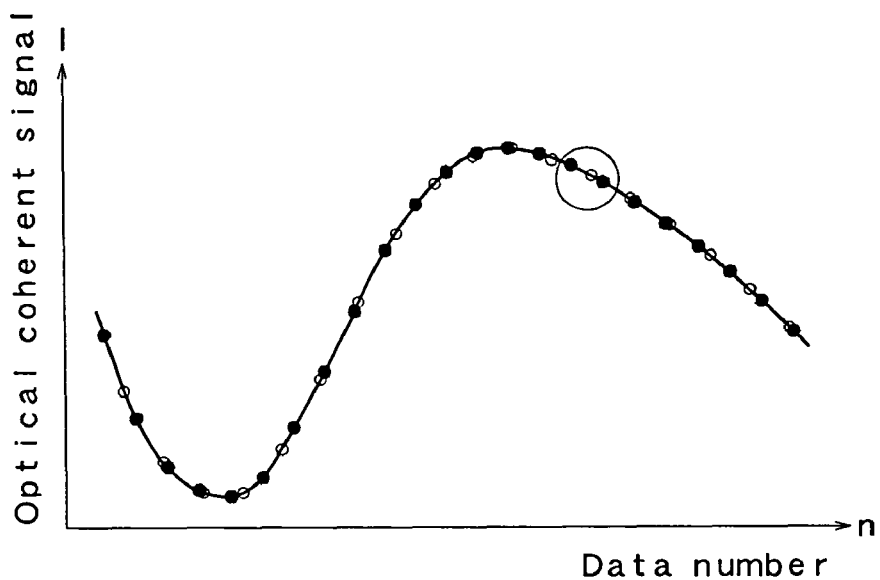
F I G. 6B
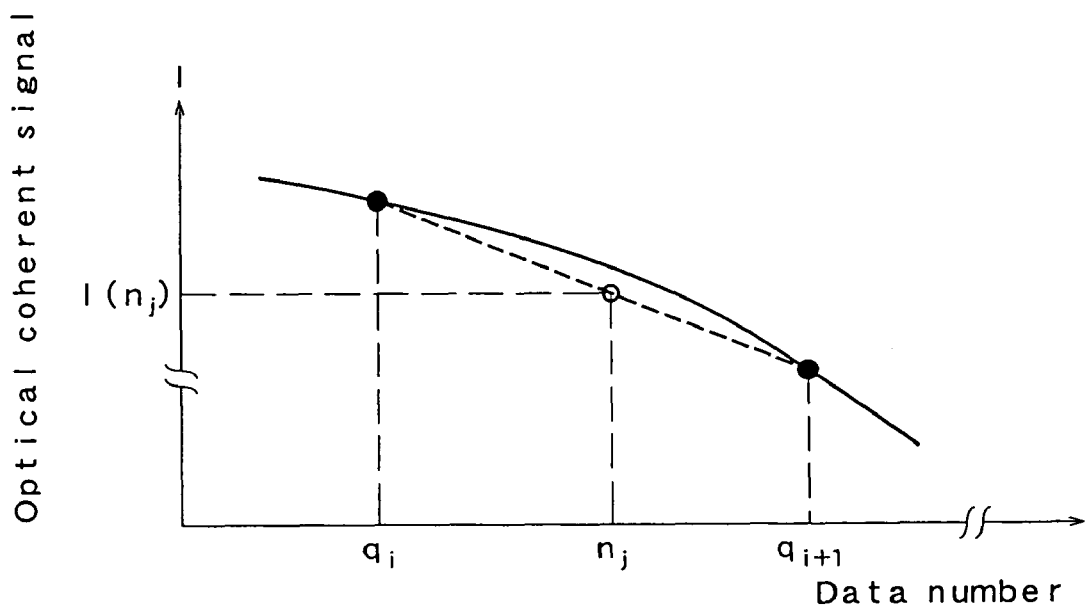

F I G. 7
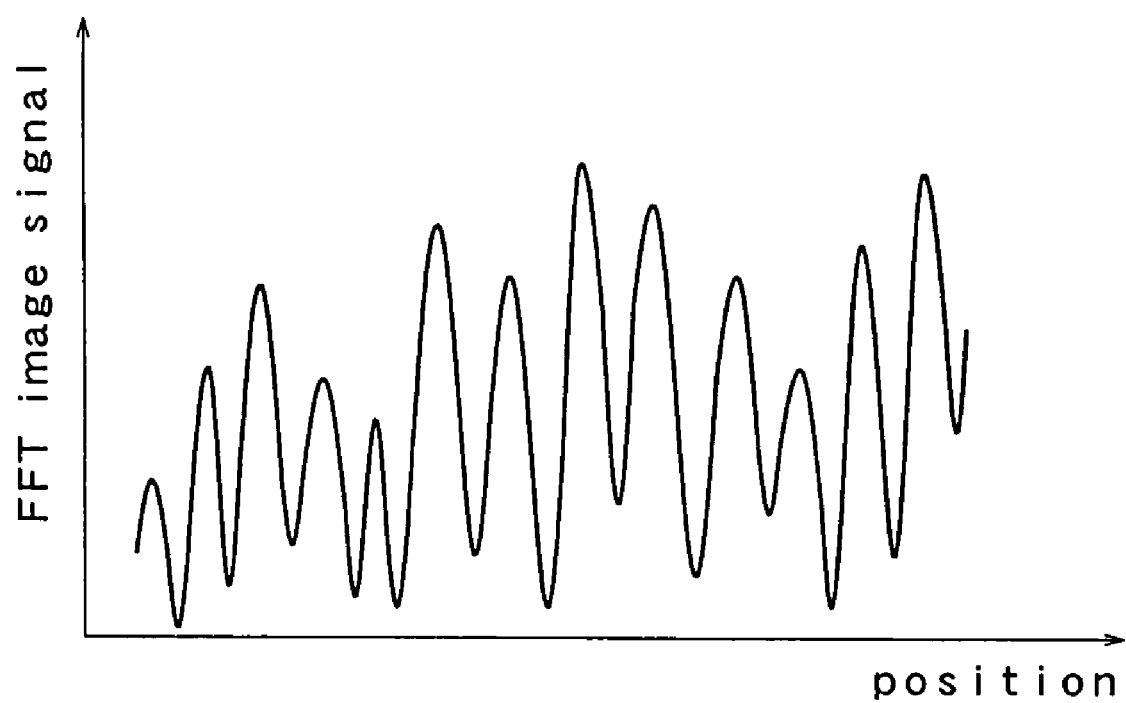

F I G. 9 B
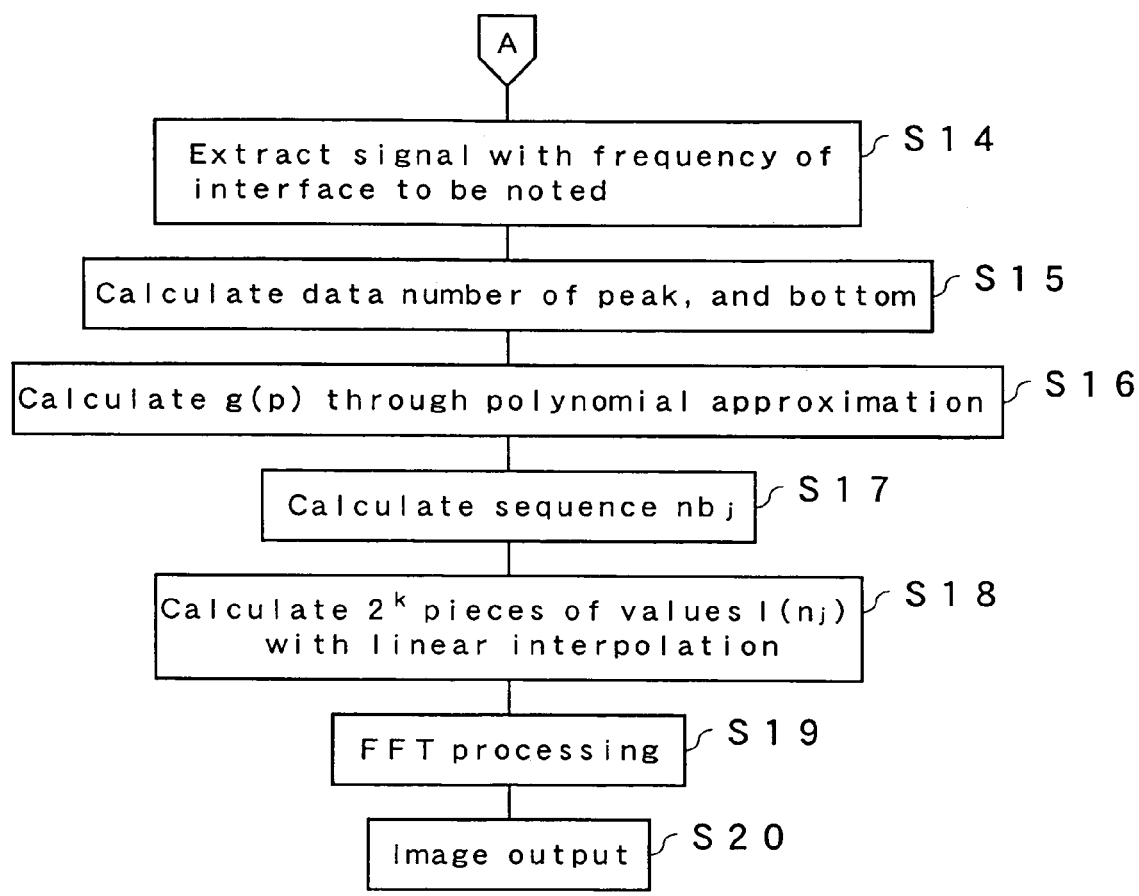

OPTICAL COHERENCE TOMOGRAPHY SYSTEM AND OPTICAL COHERENCE TOMOGRAPHY METHOD

BACKGROUND OF THE INVENTION

1. Field of the Invention

The present invention relates to an optical coherence tomography system and optical coherence tomography method for observing an image of internal structure of an object below its surface or a tomogram of lower epidermis of a biomedical tissue.

2. Discussion of the Related Art

In recent years, with the advancement of medical technique such as endoscopic therapy, there is a demand for a method of diagnosing pathological tissues non-invasively in real time. Conventionally, for example, an electronic endoscope using a CCD and imaging using CT, MRI and ultrasonic waves are used as diagnosis methods. However, the use of electronic endoscope is limited to observation of the surface of a living body. The image diagnosis system using CT, MRI or ultrasonic waves has a technical limitation in observing a target with resolution of the order of micron. To solve such problems, the light interference tomographic measurement technique has attracted attention.

The interference tomographic measurement technique has two types: time domain tomographic measurement and frequency domain tomographic measurement. The frequency domain tomographic measurement has two types: a spectrometer type and tunable light source type. Handbook of Optical Coherence Tomography, p 41-43, Mercel Dekker, Inc. 2002 discloses a measurement system using a tunable light source. The system irradiates a living body with light, continuously changes the wavelength of irradiation light, allows reference light to interfere the light with reflected light returned from a different depth in the living body with an interferometer and analyzes a frequency component of the interference signal to obtain a tomogram. This technique is expected as an advanced system because a tomogram of extreme high resolution can be created based on frequency analysis of the signal sent from the inside of the object. This system is suitable for practical use such as endoscope in that it has high sensitivity of measurement and is resistant to dynamic noise. As wavelength scanning band of the reflection light is larger, frequency analysis band is increased and thus, the resolution in a depth direction is increased.

In an optical coherence tomography device, it is necessary to obtain many points at a regular frequency interval according to resolution of the image in one wavelength scanning and set them as timing signals for Fourier transforming. The timing signal is generally referred to as a k trigger. An interval of a trigger signal corresponds to the range of observed depth, and as the interval is smaller, deeper analysis can be performed. The interval of a trigger signal must be a regular frequency interval. If the interval of the trigger signal is not an equal frequency interval, this causes a problem in that wavelength scanning becomes nonlinear resulting in generating a image with distortion or noise.

The normal wavelength-tunable laser light source, however, has a defect that wavelength does not linearly vary with respect to time, and thus, the trigger signal cannot be easily obtained at a regular frequency interval. Conventionally, as disclosed in R. Huber. et al. "Three-dimensional and C-mode OCT imaging with a compact, frequency swept laser source at 1300 nm", 26 Dec. 2005/Vol. 13, No. 26/OPTICS EXPRESS 10523, in addition to an interferometer for causing interference with back scattered light from a sample, an optical system for generating the interference signal, such as other interferometers and Fabry-Perot etalon is annexed. It is common to carry out an interference processing of the sample and frequency calibration of the interference signal of the actual sample through the annexed optical system.

The device disclosed in the latter document, however, has problems that the annexed optical system is expensive and an expensive A/D board is required.

SUMMARY OF THE INVENTION

In consideration of the above-mentioned problems, an object of the present invention is to provide an optical coherence tomography system which can display an image with high resolution by Fourier transforming at any point of regular frequency interval of a laser light source.

An optical coherence tomograpy system of the present invention comprises: a tunable light source for scanning optical emission wavelength periodically; an optical interferometer for dividing light from said tunable light source into reference light and irradiation light to an object and for generating coherent light of reflected light from the object and the reference light; a light receiving element for receiving the coherent light obtained by said optical interferometer to obtain a beat signal; and a signal processor for: fetching the beat signal of said light receiving element and assigning data numbers to the output at a regular time interval when a reflector is disposed at a measurement position of the object; calculating data numbers giving peaks of said beat signal; calculating an approximated curve showing data numbers with respect to said peak numbers; dividing variation in said peak number into any number; calculating data numbers corresponding to the divided peak number according to said approximated curve to acquire a data acquisition sequence; calculating a signal level at timing of each term of said data acquisition sequence from an output obtained by said light receiving element at a regular time interval when the measured object is disposed at the measurement position; and calculating a tomogram of said object by Fourier transforming the data obtained at a regular frequency interval.

An optical coherence tomography system of the present invention comprises: a tunable light source for scanning optical emission wavelength periodically; an optical interferometer for dividing light from said tunable light source into reference light and irradiation light to an object and for generating coherent light of reflected light from the object and the reference light; a light receiving element for receiving the coherent light obtained by said optical interferometer to obtain a beat signal; and a signal processor for: fetching the beat signal of said light receiving element and assigning data numbers to the output at a regular time interval when a reflector is disposed at a measurement position of the object; calculating data numbers giving peaks of said beat signal; calculating a first approximated curve showing data numbers with respect to said peak numbers; dividing variation in said peak number into any number; calculating data numbers corresponding to the divided peak number according to the first approximated curve to acquire a sequence; calculating a signal level at timing of each term of said sequence from an output obtained by said light receiving element at a regular time interval when the measured object is disposed at the measurement position; extracting a signal having frequency with respect to an interface to be noted from the calculated data sequence; calculating a second approximated curve showing a data number with respect to a peak number of the extracted signal; dividing variation in said peak number into any number; calculating a data number corresponding to a divided peak number according to said second approximated curve to acquire a data acquisition sequence; calculating a signal level at timing of each term of said data acquisition sequence from an output obtained by said light receiving element at a regular time interval when the measured object is disposed at the measurement position; and calculating a tomogram of said object by Fourier transforming the data obtained at a regular frequency interval.

In the optical coherence tomography system, the number of terms of said data acquisition sequence may be exponentiation of 2, and said Fourier transform may be fast Fourier transform.

In the optical coherence tomography system, said optical interferometer may include first and second optical fibers having a branching/combining part in the midpoint thereof, said first optical fiber may guide light emitted from said tunable light source to a reference mirror via said branching/combining part and guides light reflected on the reference mirror to the branching/combining part, said second optical fiber may guide light emitted from said tunable light source from said branching/combining part to a measured target, guides reflected light from the measured target to the branching/combining part again and transfer obtained coherent light to said light receiving element via said branching/combining part.

An optical coherence tomography method in an optical coherence tomography system comprises: a tunable light source for scanning optical emission wavelength periodically; an optical interferometer for dividing light from said tunable light source into reference light and irradiation light to an object and for generating coherent light of reflected light from the object and the reference light; and a light receiving element for receiving the coherent light obtained by said optical interferometer to obtain a beat signal; the method comprises steps of: fetching the beat signal of said light receiving element while assigning data numbers to the output at a regular time interval when a reflector is disposed at a measurement position of the object; calculating the data number giving a peak of said beat signal; calculating an approximated curve showing data numbers with respect to said peak numbers; dividing variation in said peak number into any number; calculating data numbers corresponding to the divided peak number according to said approximated curve to acquire a data acquisition sequence; calculating a signal level at timing of each term of said data acquisition sequence from an output obtained by said light receiving element at a regular time interval when the measured object is disposed at the measurement position; and calculating a tomogram of said object by Fourier transforming the data obtained at a regular frequency interval.

An optical coherence tomography method in an optical coherence tomography system comprises: a tunable light source for scanning optical emission wavelength periodically; an optical interferometer for dividing light from said tunable light source into reference light and irradiation light to an object and for generating coherent light of reflected light from the object and the reference light; and a light receiving element for receiving the coherent light obtained by said optical interferometer to obtain a beat signal; the method comprises steps of: fetching the beat signal of said light receiving element while assigning data numbers to the output at a regular time interval when a reflector is disposed at a measurement position of the object; calculating the data number giving a peak of said beat signal; calculating a first approximated curve showing data numbers with respect to said peak numbers; dividing variation in said peak number into any number and calculating data numbers corresponding to the divided peak number according to the first approximated curve to acquire a sequence; calculating a signal level at timing of each term of said data acquisition sequence from an output obtained by said light receiving element at a regular time interval when the measured object is disposed at the measurement position, extracting a signal having frequency with respect to an interface to be noted from the calculated data sequence; calculating a second approximated curve showing a data number with respect to a peak number of the extracted signal; dividing variation in said peak number into any number and calculating the data number corresponding to the divided peak number according to said second approximated curve to acquire a data acquisition sequence; calculating a signal level at timing of each term of said data acquisition sequence from an output obtained by said light receiving element at a regular time interval when the measured object is disposed at the measurement position; and calculating a tomogram of said object by Fourier transforming the data obtained at a regular frequency interval.

In the optical coherence tomography method, the number of components of said data acquisition sequence may be exponentiation of 2, and said Fourier transform may be fast Fourier transform.

According to the present invention having such characteristic, because of Fourier transforming at a frequency interval by processing in a signal processor, sampling at a regular interval can be carried out with high accuracy. For this reason, a tomogram with less distortion and noise can be obtained.

BRIEF DESCRIPTION OF THE DRAWINGS

FIG. 5 is a graph showing variation in a data number with respect to peak number n;

FIG. 6A is a graph showing variation in a light interference signal with respect to a data number when a measured object is disposed;

FIG. 6B is a partial enlarged view of FIG. 6A;

FIG. 7 shows an output after Fourier transforming in accordance with the present embodiment;

FIG. 9B is the other of the flow chart showing algorithm of tomogram of the tunable optical coherence tomography system in accordance with embodiment 2 of the present invention;

DESCRIPTION OF THE PREFERRED EMBODIMENTS

Embodiment 1

Figure 1:
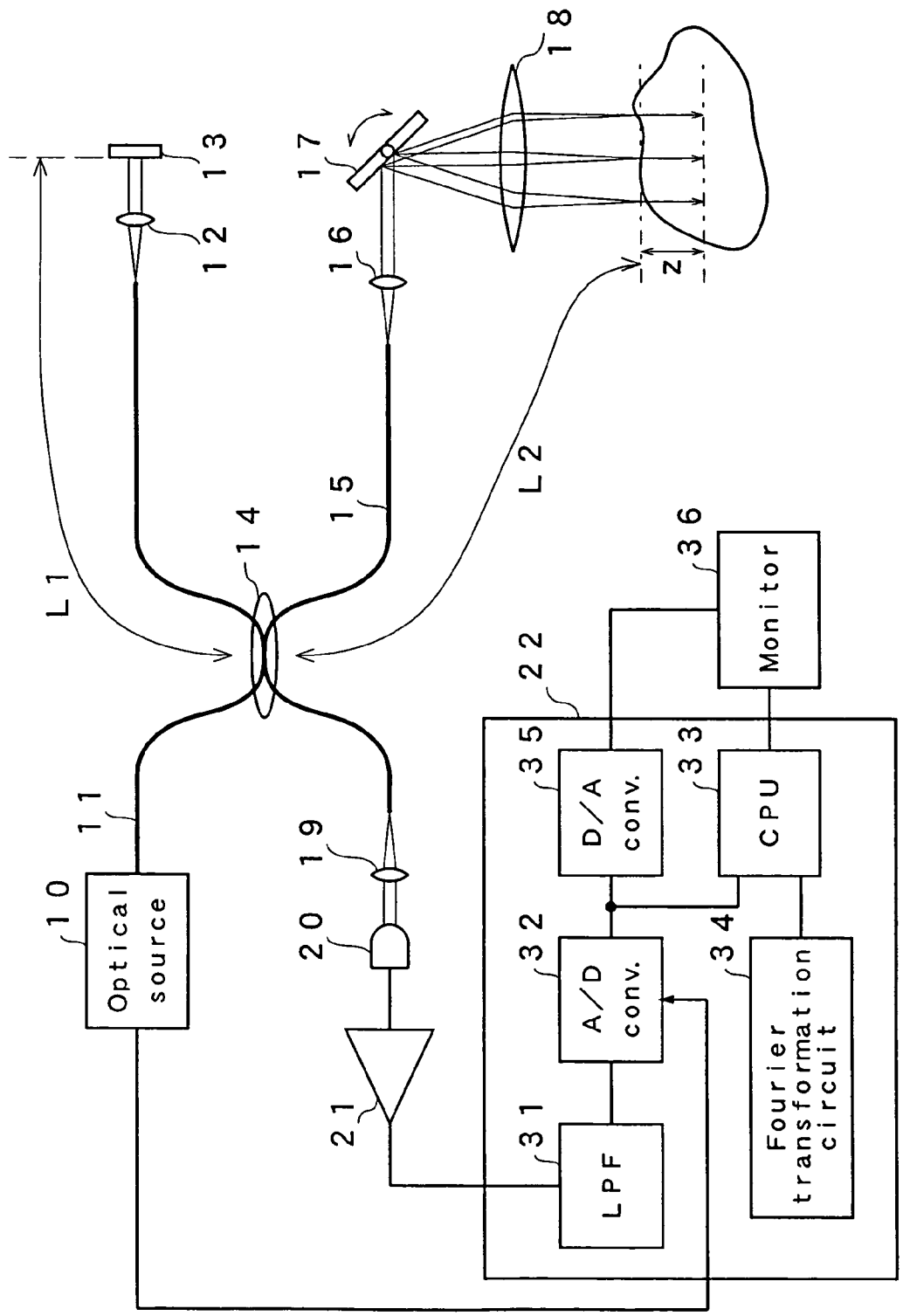
FIG. 1 is a block diagram showing an overall configuration of a tunable optical coherence tomography system in accordance with embodiment 1 of the present invention.

FIG. 1 is a block diagram showing an overall configuration of a tunable optical coherence tomography system in accordance with embodiment 1 of the present invention. In this figure, a light source 10 is a tunable light source for generating an optical signal in a certain frequency range such as 220 to 250 THz and an output thereof is sent to an optical fiber 11. A collimator lens 12 and reference mirror 13 are provided at the other end of the optical fiber 11. A branching/combining part 14 which makes the optical fiber 11 to get close to and interfere with another optical fiber 15 is provided at the midpoint of the optical fiber 11. A collimator lens 16 for converting an optical signal obtained from the tunable light source 10 via the branching/combining part 14 into a parallel beam and a scanning mirror 17 for scanning light are provided at one end of the optical fiber 15. A lens 18 for irradiating a measured object with light is provided at a position where reflected light on the scanning mirror 17 is received. The scanning mirror 17 rotates about an axis perpendicular to the paper surface in a certain range, thereby changing a reflection angle of the parallel beam and scanning a light convergence position in a horizontal direction. A photodiode 20 is connected to the other end of the optical fiber 15 via a lens 19. The photodiode 20 is a light receiving element which receives coherent light of the reflected light on the reference mirror 13 and light reflected at a measured area, thereby obtains a beat signal as an electric signal. Here, the optical fibers 11, 15, branching/combining part 14, collimator lens 12, reference mirror 13, collimator lens 16, scanning mirror 17 and lens 18 constitute an optical interferometer.

An output of the photodiode 20 is inputted to a signal processor 22 via an amplifier 21. The tunable light source 10, as described below, generates a trigger signal at the start of scanning of light and sends the trigger signal to the signal processor 22. As shown in the figure, the signal processor 22 includes a low-pass filter (LPF) 31 for removing aliasing distortion of a light interference signal. The low-pass filter 31 gives an output to an A/D converter 32. The A/D converter 32 performs A/D conversion at a predetermined regular time interval and outputs an output thereof to a CPU 33. The CPU 33 holds the data, allows a Fourier transform circuit 34 to Fourier transform based on below-mentioned algorithm and outputs an image thus obtained to a monitor 36. A D/A converter 35 generates a sawtooth image sweep signal based on the trigger signal output from the A/D converter 32 and outputs the signal to the CPU 33.

Next, principle of optical coherence tomography measurement using the tunable light source will be described. The light source irradiates a target object with coherent light whose optical frequency varies continuously and periodically and the optical interferometer allows back scattered light reflected in the object or a lower epidermis of a biological tissue to interfere with reference light. By measuring intensity distribution of the coherent light and then, measuring variation in an intensity distribution corresponding to variation in the optical frequency, a tomogram along a depth direction can be created. Furthermore, by scanning the object with a space beam one-dimensionally and two-dimensionally, two-dimensional and three-dimensional tomograms can be created.

In the optical interferometer, when two optical paths from the branching/combining part 14, that is, an optical path L1 between the branching/combining part 14 and the reference mirror 13 and an optical path L2 between the branching/combining part 14 and the reflection plane of the object are the same as each other in length, beat frequency of the coherent light becomes zero. In the event that reflected light is reflected from a depth z in the object, when the optical frequency varies in time, there occurs difference between the frequency of the reflected light on the object and the reflected light on the reference mirror 13 by the difference between the optical paths, generating beat in the coherent light. For example, given that the optical frequency of the light source is linearly scanned in time, the surface of the object is located at a position where the optical paths of the interferometer are the same in length and the reflection plane of the object is located at a depth z from the surface. In this case, since there is a certain difference between the frequency of the reference light and the reflected light on the object (object light) in the branching/combining part 14, the coherent light received by the photodiode 20 varies with certain beat frequency.

In fact, since the reflected light is generated at different contiguous positions along a depth in the object, the reflected light has different beat frequency components corresponding to the respective depths. Thus, by frequency-analyzing variation in the intensity of the coherent light, the intensity of the reflected light from a particular depth corresponding to the beat frequency can be detected. A tomogram can be generated by acquiring spatial distribution of the reflection intensity.

Figure 2:
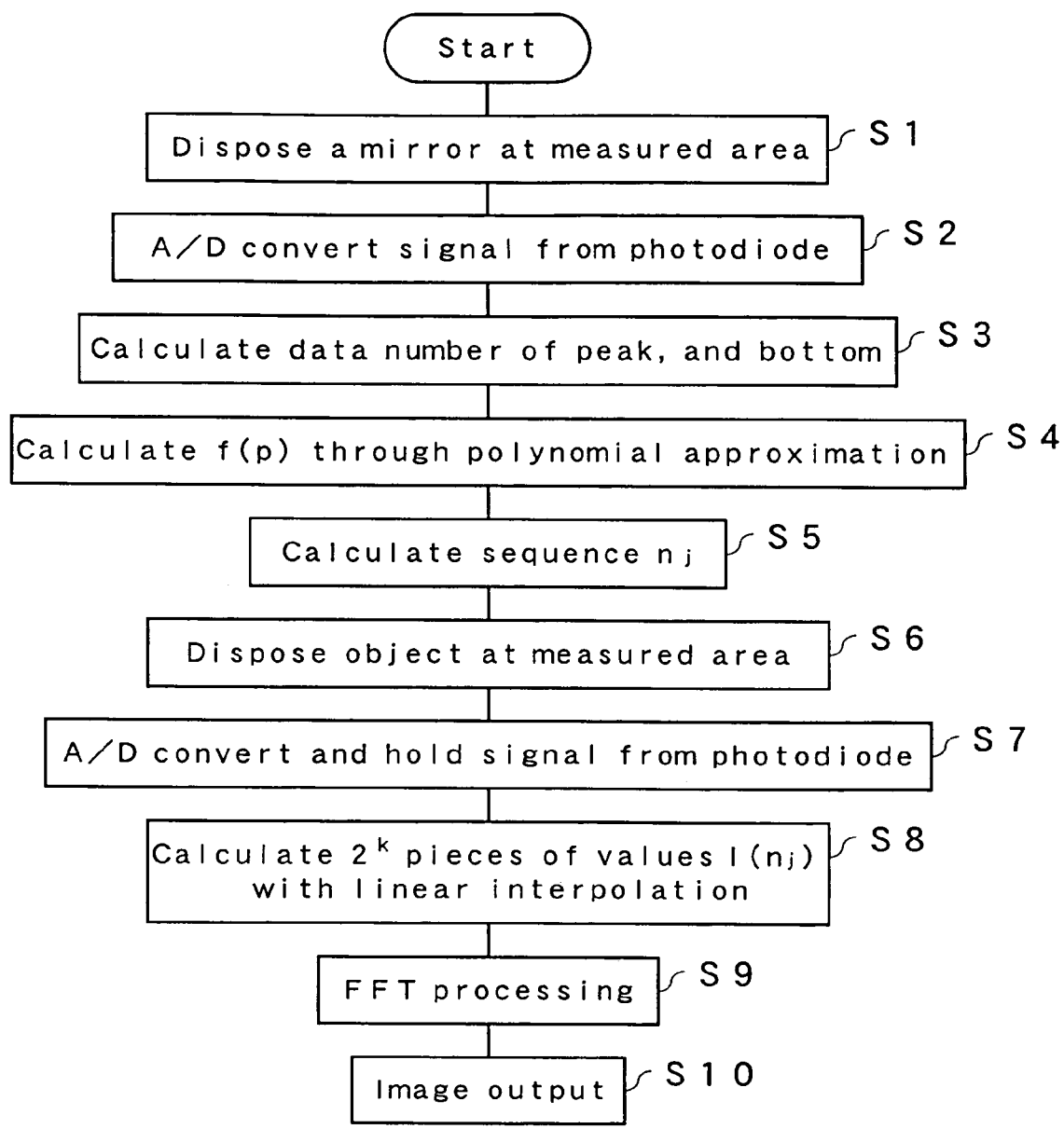
FIG. 2 is a flow chart showing algorithm of tomographic display in accordance with the present embodiment.
Figure 3:
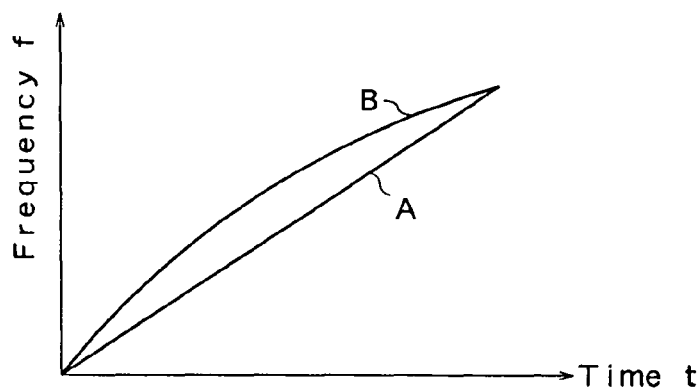
FIG. 3 is a graph showing an example of relationship between scanning time and oscillatory frequency of a laser light source in accordance with the present embodiment.

A display algorithm of the optical coherence tomography system in accordance with the present embodiment will be described using a flow chart in FIG. 2. First, it is preferred that the tunable light source 10 is a light source whose frequency f linearly varies with respect to time as represented by a straight line A in FIG. 3. Actually, however, the frequency f nonlinearly varies with respect to time t as represented by a curved line B. If sampling is simply carried out by a clock trigger at a regular time interval using the light source, distortion of an image or noise occurs in accordance with the degree of nonlinearity of wavelength scanning.

Then, the algorithm for correcting the characteristic of the light source and displaying the tomogram without distortion will be described. First, given that a distance between the branching/combining part 14 and the reference mirror 13 is defined as L1, a reflector such as a mirror is disposed in a measured area at a position away from the branching/combining part 14 by a distance L2 which is different from L1, and a difference between the optical paths L1 and L2 is defined as ΔL (Step S1).

Figure 4:
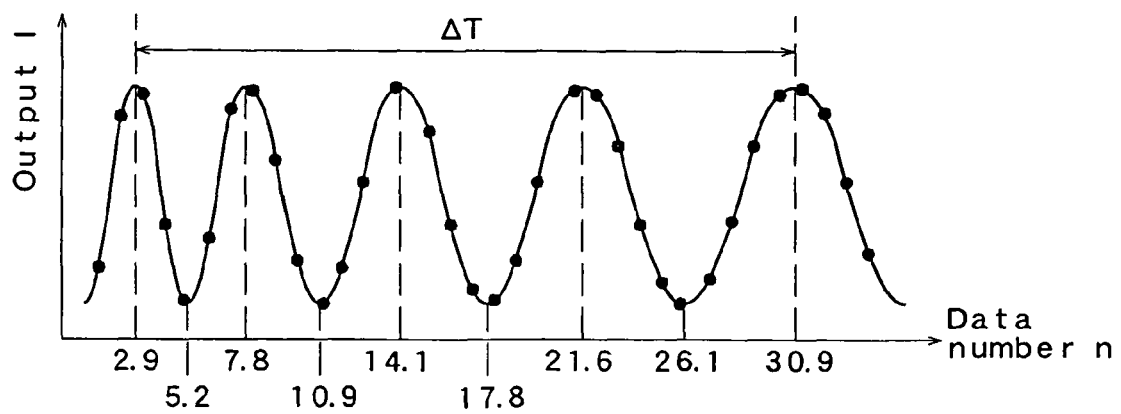
FIG. 4 is a graph showing variation in a light interference output with respect to a data number in the present embodiment.

Then, the tunable light source 10 is driven and an output from the photodiode 20 is A/D converted by the A/D converter 32 at a regular time interval (Step S2). FIG. 4 shows variation in a light interference signal from the photodiode 20, and black points represent timing of A/D conversion at a regular interval. Since A/D conversion values are obtained as data at timing of the black points, data numbers 1, 2, . . . are given to the data. A horizontal axis in FIG. 4 represents time t in the unit n of the data numbers. Since the A/D converter 32 performs A/D conversion at a regular interval, even when the cycle of the waveform continuously varies as shown in FIG. 4, a discrete output is obtained at timing of A/D conversion at a regular time interval. Time at a peak and bottom (hereinafter, referred to as peak) position of an output from the photodiode 20 is calculated in the unit of data number from the data number and A/D conversion value according to a least-squares method or the like (Step S3). In this manner, a relative time sequence giving top and bottom peak position is acquired. For example, in a case in FIG. 4, time at a first peak value is represented by a data number of 2.9, time at a second peak value is represented by a data number of 5.2 and time at third, fourth, . . . peak values are represented by data numbers of 7.8, 10.9, . . . , respectively. Here, each peak is represented by a peak number p. Then, the data in FIG. 4 is inputted to FIG. 5 where a horizontal axis represents peak number p at a regular interval and a vertical axis represents time n in the unit of data number. An equation connecting points to one another is acquired according to polynomial approximation to obtain an approximated curve f(p) (Step S4). For simplification of description, FIG. 4 shows only peaks and bottoms from 1 to 10. However, in fact, the approximated curve f(p) is acquired from, for example, a few hundreds of pieces of data. Hereinafter, a maximum value of the peak number is set to P. The approximated curve f(p) is a transformation equation for transforming regular time interval of the vertical axis into regular frequency interval of the horizontal axis.

In FIG. 5, the horizontal axis represents the peak number p, the vertical axis represents the data number n corresponding to time when data is acquired, and ΔP represents a difference in the peak number between start of measurement and a maximum value P of the peak number. Then, the ΔP is divided into the number of points J for fast Fourier transforming (FFT). The number of points J for FFT is exponentiation of 2 i.e. $2^k$, where k is a natural number. For example, J is 2048 ($=2^{11}$) and the variable j changes from 0 to J−1. A sequence $p_j$ including following terms obtained by dividing ΔP is calculated.

$$p_0 = (\Delta P/J) \times 0$$
$$p_1 = (\Delta P/J) \times 1$$
$$p_2 = (\Delta P/J) \times 2$$
$$\vdots$$
$$p_{J-1} = (\Delta P/J) \times (J-1)$$

Next, $p_j$ (j=0 to J−1) thus obtained are substituted into the approximated curve f(p) shown in FIG. 5.

$$f(p_j) = n_j$$

In this manner, a value $n_j$ which corresponds to the data number corresponding to each $p_j$ is acquired. Thereby, a J terms sequence of the data number $n_j$ at a regular frequency interval, here, 2048 terms ($n_0$ to $n_{2047}$) are acquired (Step S5). The sequence of $n_j$ is referred to as a data acquisition sequence.

Next, in a state where a reflector such as a living tissue to be actually measured is disposed at a measured area, the tunable light source 10 is driven (Step S6). Thus, coherent light of the light reflected on the reference mirror 13 and the reflected light from the object interfere with each other at the branching/combining part 14 and the beat frequency is obtained as an electric signal by the photodiode 20. FIG. 6A is a diagram showing an example of the output obtained from the photodiode 20. Here, as in the above-mentioned case, the light interference signal is A/D converted and held (Step S7). Timings at this time are made at a regular time interval and represented as black circles in the figure. A data number at a regular time interval is sequentially defined as $q_0$, $q_1$, . . . . Optic signal levels (represented as white circles in the figure) corresponding to a data number $n_j$ at the above-mentioned time taken at a regular frequency interval is calculated from the values and A/D conversion values according to a linear interpolation or the like. FIG. 6B is an enlarged view of the state of detecting data numbers $q_i$, $q_{i+1}$ before/after $n_j$ and calculating the signal level $I(n_j)$ of the coherent light at this time according to linear interpolation. In this manner, as shown in FIG. 6A, values $I(n_0)$ to $I(n_{2047})$ of the optical signals of all $n_j$, that is, $n_0$, $n_1$, $n_2$ . . . $n_{2047}$ are acquired (Step S8). Based on 2048 pieces of data thus acquired, an FFT operation is performed by the fast Fourier transform circuit 34 (Step S9). In this state, it is deemed that, as shown by a curve A in FIG. 3, characteristic of variation in waveform of the light source is linearly corrected. By doing so, as shown in FIG. 7, an image signal on the position to the object can be acquired. Thereby, an one-dimensional image can be obtained. Furthermore, by scanning light by use of the scanning mirror 17, the image can be made a two-dimensional image.

Figure 8:
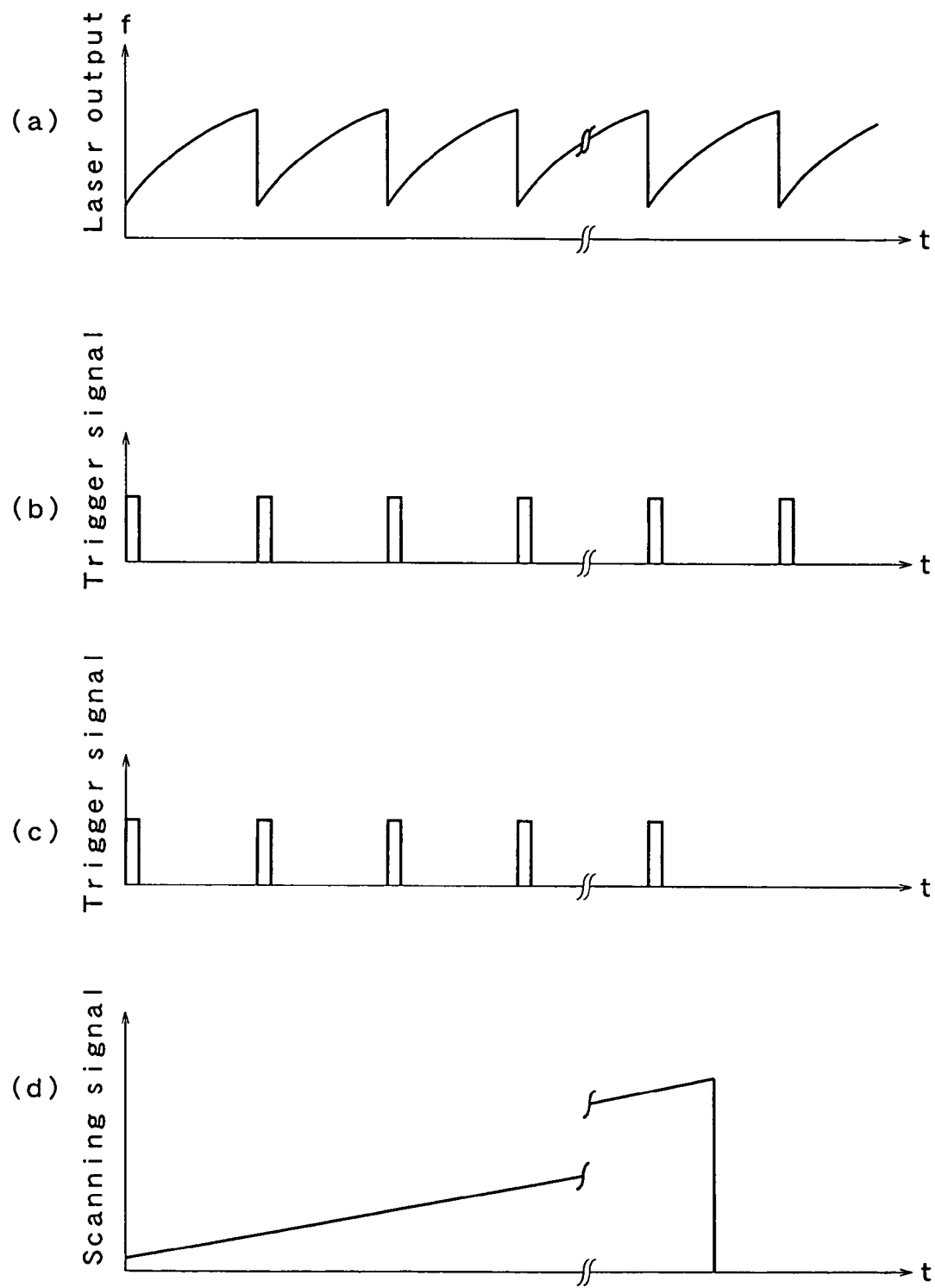
FIG. 8 is a time chart showing variation in an image signal with respect to a position after FFT processing.

FIG. 8 is a time chart showing overall operation of the optical tomogram display system. In FIG. 8, (a) shows relationship between the frequency f of laser beam emitted from the tunable light source and time. As shown (b) in FIG. 8, a trigger signal is obtained from the tunable light source 10 at the timing of start of sawtooth wavelength scanning. This signal is sent to the A/D converter 32. The A/D converter 32 starts A/D conversion at predetermined time interval according to the trigger signal. The trigger signal for start of scanning while A/D conversion is started is outputted as shown (c) in FIG. 8. The D/A converter 35 outputs a sawtooth signal for changing the image based on the trigger signal as shown in (d) FIG. 8. The sawtooth signal is sent to the monitor 36 along with the image signal calculated by the CPU. Thus, a two-dimensional image signal can be outputted on the monitor 36.

Embodiment 2

Figure 9A:
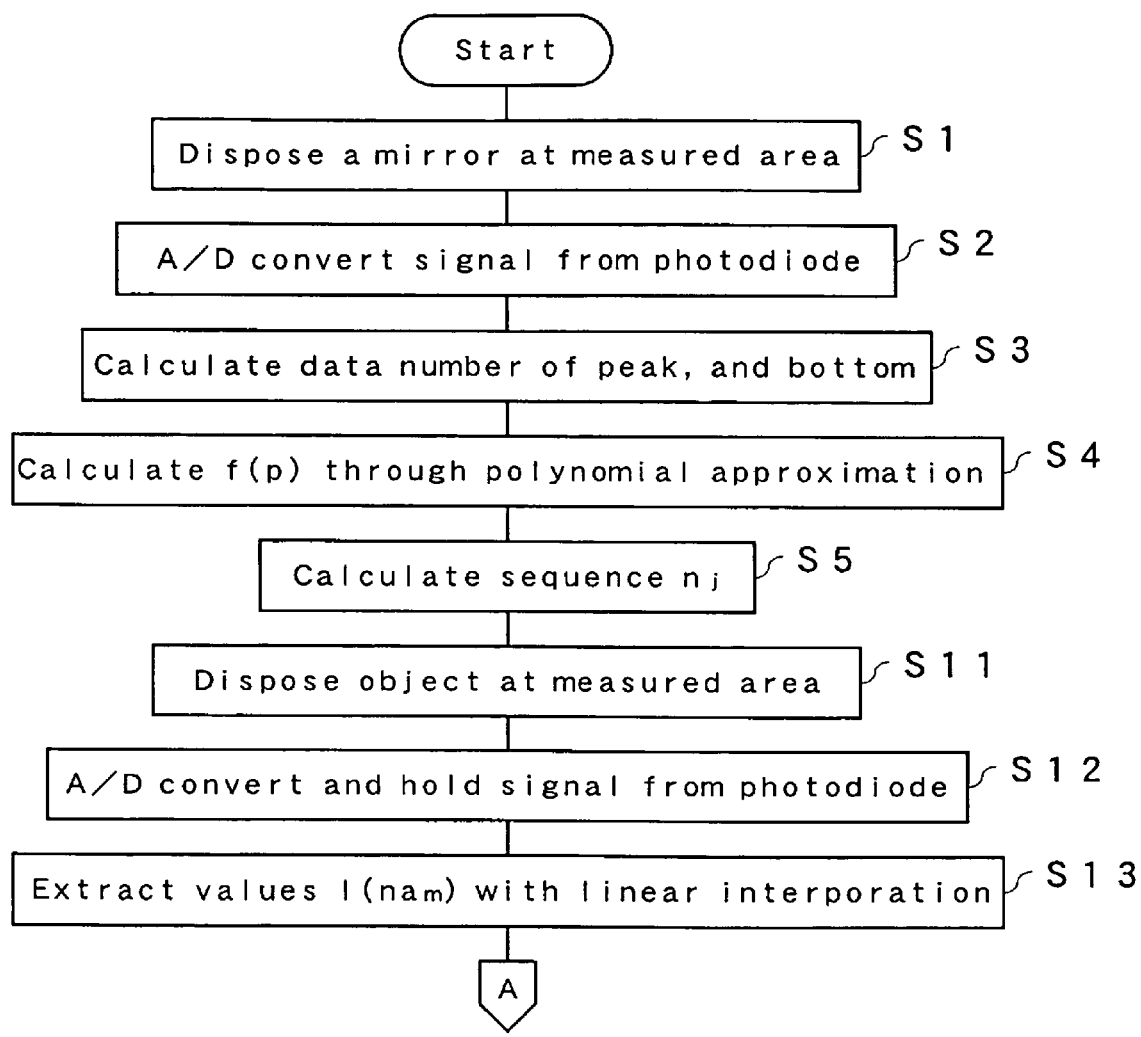
FIG. 9A is a half of a flow chart showing algorithm of tomogram of a tunable optical coherence tomography system in accordance with embodiment 2 of the present invention.
Figure 10:
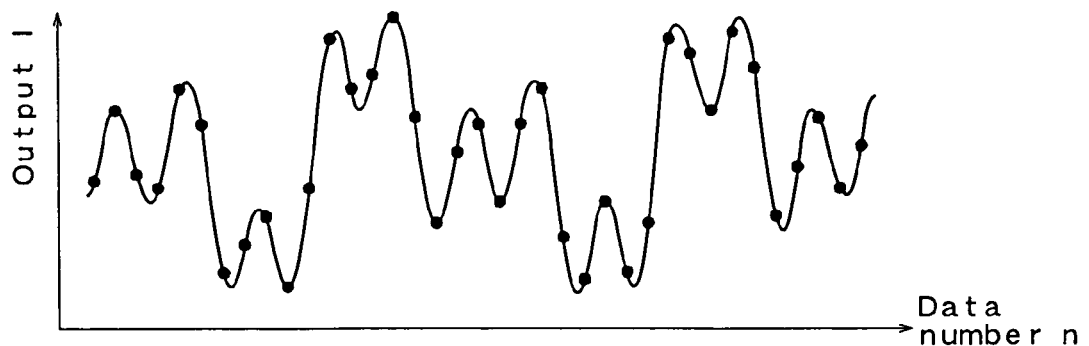
FIG. 10 is a graph showing variation in a light interference output with respect to a data number in accordance with the present embodiment.

Next, an optical coherence tomography system in accordance with embodiment 2 of the present invention. Overall block diagram is the same as that in embodiment 1. According to algorithm in the present embodiment, an error due to wavelength dispersion caused by variation in the refractive index of the object to be measured depending on wavelength is removed. Operations in the present embodiment will be described referring to a flow chart of FIGS. 9A and 9B. Steps S1 to S5 in the present embodiment are the same as those in embodiment 1. Here, the sequence at Step S5 is defined as $na_m$ (m=0 to M−1). Subsequently, at Step S11, a measured object or a similar sample as a measured target is disposed at a measurement point. Here, the measured target itself is disposed. Subsequently, at Step S12, the light coherent signal is detected and the A/D conversion value is held. Furthermore, at Step 13, as in the above-mentioned Step S8, the A/D conversion value is extracted at each timing of $na_m$ according to straight-line approximation to acquire the light coherent signal $I(na_m)$. In this case, M is not necessarily exponentiation of 2 and may be any integer. FIG. 10 is a graph showing variation in the light interference signal thus obtained.

Figure 11:
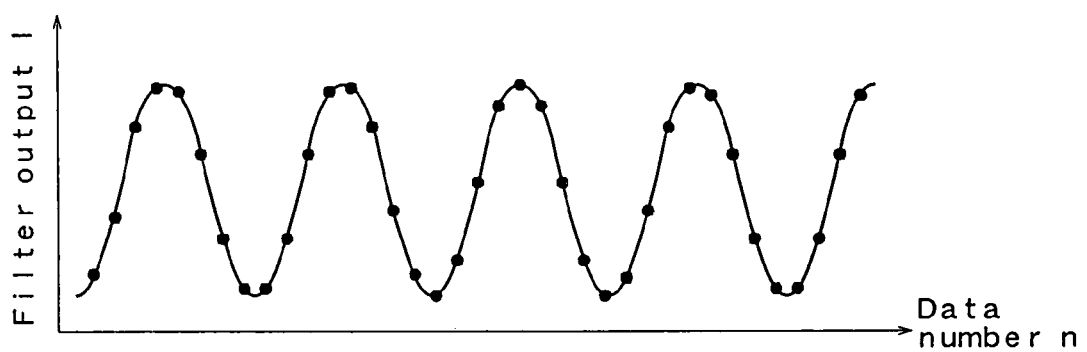
FIG. 11 is a graph showing variation in an output with respect to the data number after filtering.

Then, at Step S14 in FIG. 9B, frequency corresponding to an interface to be noted is extracted. For example, when the measured target is a human body, there occurs reflection on the skin surface or the inside of the body. When the image to be noted corresponds to the reflection on the inside of the body, not the skin surface, corresponding frequency is extracted by a band-pass filter. Here, filtering of software is carried out by the CPU 33. FIG. 11 is a graph showing variation in an output thus obtained. In FIG. 11, a horizontal axis represents data number n. The cycle is approximately regular, but slightly changes due to wavelength dispersion.

Figure 12:
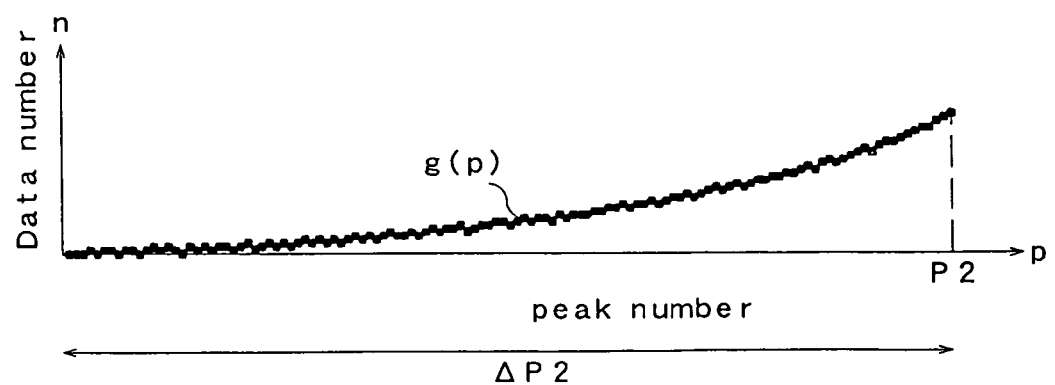
FIG. 12 is a view showing relationship between a peak number and the data number.

Next, at Step S15, peak values are calculated from this graph according to the least-squares method. At Step S16, as in Steps S3 and S4, as shown in FIG. 12, peak values are plotted using peak number in a horizontal axis and data number in a vertical axis. Then, an approximated curve g(p) is calculated as a function of the data number with respect to the peak number p according to polynomial approximation. Here, a maximum value of the peak number is set to P2 and variation in the peak number is set to ΔP2. As in Step S5, a sequence $nb_j$ is acquired from g(p). As mentioned above, the number of pieces of data J is defined as exponentiation of 2, i.e. $2^k$. For example J is 2048 for FFT processing. Consequently, the sequence contains 2048 terms from $nb_0$ to $nb_{2047}$. The sequence is referred to as data acquisition sequence.

As in Step S8, 2048 and the like pieces of data are extracted from the held output at the timing of data acquisition sequence $nb_j$ according to straight-line approximation. Then, at Step S17, FFT processing is carried out based on the data to output an image. Thus, it is possible to obtain data without any error due to wavelength dispersion of the sampled or an actual measured object and thus, generate a two-dimensional image more accurately.

Although the two-dimensional image data is obtained in each of the above-mentioned embodiments, a three-dimensional image can be obtained by rotating the scanning mirror 17 in a direction perpendicular to a paper surface of FIG. 1 as well as about an axis parallel to the paper surface. Furthermore, an optical output level may be doubled by using a balanced photodetector as the photodiode 20. Although J is exponentiation of 2 for FFT in the above-mentioned embodiments, J is not limited to exponentiation of 2 in the case of DFT.

It is to be understood that although the present invention has been described with regard to preferred embodiments thereof, various other embodiments and variants may occur to those skilled in the art, which are within the scope and spirit of the invention, and such other embodiments and variants are intended to be covered by the following claims.

The text of Japanese priority application No. 2007-105749 filed on Apr. 13, 2007 is hereby incorporated by reference.

What is claimed is:

1. An optical coherence tomography system comprising:
    a tunable light source for scanning optical emission wavelength periodically;
    an optical interferometer for dividing light from said tunable light source into reference light and irradiation light to an object and for generating coherent light of reflected light from the object and the reference light;
    a light receiving element for receiving the coherent light obtained by said optical interferometer to obtain a beat signal; and
    a signal processor for: fetching the beat signal of said light receiving element and assigning data numbers to an output from said light receiving element at a regular time interval when a reflector is disposed at a measurement position of the object; calculating data numbers based on peaks of said beat signal and assigning a peak number to each of the peaks; calculating an approximated curve showing data numbers with respect to said peak numbers; dividing variation in said peak number into any number; calculating data numbers corresponding to the divided peak number according to said approximated curve to acquire a data acquisition sequence; calculating a signal level at a timing of each data number of said data acquisition sequence from an output obtained by said light receiving element at a regular time interval when the measured object is disposed at the measurement position; and calculating a tomogram of said object by Fourier transforming the calculated signal level of a regular frequency interval.

2. The optical coherence tomography system according to claim 1, wherein
    the number of terms of said data acquisition sequence is exponentiation of 2, and
    said Fourier transform is a fast Fourier transform.

3. The optical coherence tomography system according to claim 1, wherein
    said optical interferometer includes first and second optical fibers having a branching/combining part in the midpoint thereof,
    said first optical fiber guides light emitted from said tunable light source to a reference mirror via said branching/combining part and guides light reflected on the reference mirror to the branching/combining part,
    said second optical fiber guides light emitted from said tunable light source from said branching/combining part to a measured target, guides reflected light from the measured target to the branching/combining part again and transfer obtained coherent light to said light receiving element via said branching/combining part.

4. An optical coherence tomography system comprising:
    a tunable light source for scanning optical emission wavelength periodically;
    an optical interferometer for dividing light from said tunable light source into reference light and irradiation light to an object and for generating coherent light of reflected light from the object and the reference light;
    a light receiving element for receiving the coherent light obtained by said optical interferometer to obtain a beat signal; and
    a signal processor for: fetching the beat signal of said light receiving element and assigning data numbers to an output from the light receiving element at a regular time interval when a reflector is disposed at a measurement position of the object; calculating data numbers based on peaks of said beat signal and assigning a peak number to each of the peaks; calculating a first approximated curve showing data numbers with respect to said peak numbers; dividing variation in said peak number into any number; calculating data numbers corresponding to the divided peak number according to the first approximated curve to acquire a sequence; calculating a signal level at a timing of each data number of said sequence from an output obtained by said light receiving element at a regular time interval when the measured object is disposed at the measurement position; extracting a signal having a frequency with respect to an interface to be noted from the calculated data sequence; calculating a second approximated curve showing a data number with respect to a peak number of the extracted signal; dividing variation in said peak number into any number; calculating a data number corresponding to a divided peak number according to said second approximated curve to acquire a data acquisition sequence; calculating a signal level at a timing of each data number of said data acquisition sequence from an output obtained by said light receiving element at a regular time interval when the measured object is disposed at the measurement position; and calculating a tomogram of said object by Fourier transforming the calculated signal level of a regular frequency interval.

5. The optical coherence tomography system according to claim 4, wherein the number of terms of said data acquisition sequence is exponentiation of 2, and said Fourier transform is a fast Fourier transform.

6. The optical coherence tomography system according to claim 4, wherein said optical interferometer includes first and second optical fibers having a branching/combining part in the midpoint thereof, said first optical fiber guides light emitted from said tunable light source to a reference mirror via said branching/combining part and guides light reflected on the reference mirror to the branching/combining part, said second optical fiber guides light emitted from said tunable light source from said branching/combining part to a measured target, guides reflected light from the measured target to the branching/combining part again and transfer obtained coherent light to said light receiving element said the branching/combining part.

7. An optical coherence tomography method in an optical coherence tomography system comprising:

a tunable light source for scanning optical emission wavelength periodically;

an optical interferometer for dividing light from said tunable light source into reference light and irradiation light to an object and for generating coherent light of reflected light from the object and the reference light; and a light receiving element for receiving the coherent light obtained by said optical interferometer to obtain a beat signal;

the method for a signal processing by a signal processor, comprising steps of:

fetching the beat signal of said light receiving element while assigning data numbers to an output from said light receiving element at a regular time interval when a reflector is disposed at a measurement position of the object;

calculating the data number based on a peak of said beat signal and assigning a peak number to each of the peaks;

calculating an approximated curve showing data numbers with respect to said peak numbers;

dividing variation in said peak number into any number;

calculating data numbers corresponding to the divided peak number according to said approximated curve to acquire a data acquisition sequence;

calculating a signal level at a timing of each data number of said data acquisition sequence from an output obtained by said light receiving element at a regular time interval when the measured object is disposed at the measurement position; and calculating a tomogram of said object by Fourier transforming the calculated signal level of a regular frequency interval.

8. The optical coherence tomography method according to claim 7, wherein the number of components of said data acquisition sequence is exponentiation of 2, and said Fourier transform is fast Fourier transform.

9. An optical coherence tomography method in an optical coherence tomography system comprising:

a tunable light source for scanning optical emission wavelength periodically;

an optical interferometer for dividing light from said tunable light source into reference light and irradiation light to an object and for generating coherent light of reflected light from the object and the reference light; and a light receiving element for receiving the coherent light obtained by said optical interferometer to obtain a beat signal;

the method for a signal processing by a signal processor, comprising steps of:

fetching the beat signal of said light receiving element while assigning data numbers to an output from said light receiving element at a regular time interval when a reflector is disposed at a measurement position of the object;

calculating the data number based on a peak of said beat signal and assigning a peak number to each of the peaks;

calculating a first approximated curve showing data numbers with respect to said peak numbers;

dividing variation in said peak number into any number and calculating data numbers corresponding to the divided peak number according to the first approximated curve to acquire a sequence;

calculating a signal level at a timing of each data number of said sequence from an output obtained by said light receiving element at a regular time interval when the measured object is disposed at the measurement position, extracting a signal having a frequency with respect to an interface to be noted from the calculated data sequence;

calculating a second approximated curve showing a data number with respect to a peak number of the extracted signal;

dividing variation in said peak number into any number and calculating the data number corresponding to the divided peak number according to said second approximated curve to acquire a data acquisition sequence;

calculating a signal level at a timing of each data number of said data acquisition sequence from an output obtained by said light receiving element at a regular time interval when the measured object is disposed at the measurement position; and calculating a tomogram of said object by Fourier transforming the calculated signal level of a regular frequency interval.

10. The optical coherence tomography method according to claim 9, wherein the number of components of said data acquisition sequence is exponentiation of 2, and said Fourier transform is a fast Fourier transform.

* * * * *